(12) United States Patent
Zhang et al.

(10) Patent No.: US 12,116,345 B2
(45) Date of Patent: Oct. 15, 2024

(54) LOW-TEMPERATURE CONTINUOUS-FLOW PREPARATION METHOD OF BEDAQUILINE

(71) Applicants: SHANGHAI JIAOTONG UNIVERSITY, Shanghai (CN); SPH NO.1 BIOCHEMICAL & PHARMACEUTICAL CO., LTD., Shanghai (CN)

(72) Inventors: Wanbin Zhang, Shanghai (CN); Yaohua Zhang, Shanghai (CN); Feng Gao, Shanghai (CN); Wei Yu, Shanghai (CN); Jing Li, Shanghai (CN); Ximing Jiang, Shanghai (CN); Zhenfeng Zhang, Shanghai (CN); Liang Wu, Shanghai (CN); Yuanlin Wang, Shanghai (CN); Yujia Fu, Shanghai (CN)

(73) Assignees: SHANGHAI JIAOTONG UNIVERSITY, Shanghai (CN); SPH NO.1 BIOCHEMICAL & PHARMACEUTICAL CO., LTD., Shanghai (CN)

( * ) Notice: Subject to any disclaimer, the term of this patent is extended or adjusted under 35 U.S.C. 154(b) by 0 days.

(21) Appl. No.: 18/670,653

(22) Filed: May 21, 2024

(65) Prior Publication Data

US 2024/0308963 A1    Sep. 19, 2024

Related U.S. Application Data

(63) Continuation of application No. PCT/CN2023/138097, filed on Dec. 12, 2023.

(30) Foreign Application Priority Data

Aug. 1, 2023    (CN) .......................... 202310959686.6

(51) Int. Cl.
*C07D 215/227*    (2006.01)
*B01J 19/24*    (2006.01)

(52) U.S. Cl.
CPC ...... *C07D 215/227* (2013.01); *B01J 19/2415* (2013.01); *B01J 2219/00033* (2013.01)

(58) Field of Classification Search
CPC .................................................. C07D 215/227
See application file for complete search history.

(56) References Cited

FOREIGN PATENT DOCUMENTS

| | | |
|---|---|---|
| CN | 101180302 B | 6/2013 |
| CN | 105085395 A | 11/2015 |
| CN | 105175329 A | 12/2015 |
| CN | 105198808 A | 12/2015 |
| CN | 106866525 A | 6/2017 |
| CN | 111574444 A | 8/2020 |
| CN | 116899502 A | 10/2023 |
| WO | 2020161743 A1 | 8/2020 |
| WO | WO2024007621 * 1/2024 ......... C07D 215/227 |

OTHER PUBLICATIONS

Hlengekile Lubanyana et al., "Improved Synthesis and Isolation of Bedaquiline". ACS Omega, Feb. 17, 2020, vol. 5, No. 7, pp. 3607-3611.
Sarah Jane Mear et al., "Diastereoselectivity is in the Details: Minor Changes Yield Major Improvements to the Synthesis of Bedaquiline**", Chemistry—A European Journal, vol. 28, No. 47, Aug. 22, 2022, e202201311.
Feng Gao et al.," Asymmetric synthesis of bedaquiline based on bimetallic activation and non-covalent interaction promotion strategies", Science China Chemistry, vol. 65, No. 10, Oct. 2022, pp. 1968-1977.

* cited by examiner

*Primary Examiner* — Nizal S Chandrakumar

(57) ABSTRACT

A low-temperature continuous-flow preparation method of bedaquiline includes the following steps. (a) A first feed liquid and a second feed liquid are subjected to a first continuous flow reaction for 30-600 seconds to obtain a first reaction mixture. (b) The first reaction mixture and a third feed liquid are subjected to a second continuous flow reaction for 30-600 seconds to obtain a second reaction mixture. (c) The second reaction mixture was quenched to afford bedaquiline.

12 Claims, 11 Drawing Sheets

LOW-TEMPERATURE CONTINUOUS-FLOW PREPARATION METHOD OF BEDAQUILINE

CROSS-REFERENCE TO RELATED APPLICATIONS

This application is a continuation of International Patent Application No. PCT/CN2023/138097, filed on Dec. 12, 2023, which claims the benefit of priority from Chinese Patent Application No. 202310959686.6, filed on Aug. 1, 2023. The content of the aforementioned application, including any intervening amendments thereto, is incorporated herein by reference in its entirety.

TECHNICAL FIELD

This application relates to pharmaceutical preparation, and more particularly to a low-temperature continuous-flow preparation method of bedaquiline.

BACKGROUND

Tuberculosis (TB) is an infectious disease caused by *Mycobacterium tuberculosis*, and is the leading cause of death due to the infection of a single causative agent (about 1.6 million deaths reported per year). Bedaquiline was approved by FDA in 2012 for the treatment of multidrug-resistant and rifampicin-resistant tuberculosis (MDR/RR-TB). The anti-tuberculosis drugs were reclassified by WHO in 2018, and Bedaquiline was recognized as the first choice for the long-term treatment of MDR/RR-TB. The stereoselective construction of $Csp^3$-$Csp^3$ bond in the consecutive chiral center of Bedaquiline poses a challenge to the research and development staff, and thus the efficient industrial synthesis of Bedaquiline has not yet been achieved, which results in high price. Therefore, there is an urgent need to improve the production process and reduce the synthesis cost to make the drug affordable to low-income population.

Chinese Patent publication No. 101180302B discloses a one-step synthetic method of bedaquiline (BDQ), where 6-bromo-3-benzyl-2-methoxyquinoline is subjected to benzylic deprotonation under the action of lithium diisopropylamide (LDA) at low temperature, and then undergoes an addition reaction with 3-dimethylamino-1-naphthyl-1-acetone to obtain a mixture of four optical isomers of BDQ, which is concentrated, treated with ethanol, and subjected to chiral resolution in the presence of the chiral resolving agent (R)-binaphthol phosphate to give BDQ with a very low yield (7-9%). In addition, due to the excellent efficiency, the application of the asymmetric catalytic synthesis in the preparation of BDQ has attracted much attention. Shibasaki and Chandrasekhar both reported the construction of the first chiral carbon by asymmetric catalysis and construction of the second chiral carbon by asymmetric synthesis. However, these routes all suffer from complicated reaction process, low yield, and high cost. In addition, it has been demonstrated by a research group from South Africa in 2020 (Lubanyana H, Arvidsson P I, Govender T, Kruger H G, Naicker T. Improved Synthesis and Isolation of Bedaquiline. *ACS Omega* 2020, 5, 3607-3611) that the diastereoselectivity of BDQ can be improved to 9:1 using a C2-symmetric chiral amine ligand, and the optically-pure target compound is subsequently harvested by chiral resolution. However, this synthesis strategy did not improve the yield. Recently, Jamison et al. employed the continuous-flow chemistry synthesis to obtain a mixture of four isomers with improved yield (Mear S J, Lucas T, Ahlqvist G P, Robey J M S, Dietz J P, Khairnar P V, Maity S, Williams C L, Snead D R, Nelson R C, Opatz T, Jamison T F. Diastereoselectivity is in the Details: Minor Changes Yield Major Improvements to the Synthesis of Bedaquiline. *Chem. Eur. J.* 2022, 28, e202201311. doi: 10.1002/chem.202201311. Epub 2022 Jul. 7. PMID: 35675114; PMCID: PMC9545417), which still did not achieve the efficient synthesis of the target product. Prof Wanbin Zhang's team from Shanghai Jiaotong University proposed an asymmetric synthesis strategy of BDQ (Gao, F., Li, J., Ahmad, T. et al. Asymmetric synthesis of bedaquiline based on bimetallic activation and non-covalent interaction promotion strategies. *Sci. China Chem.* 65, 1968-1977 (2022). https://doi.org/10.1007/s11426-022-1387-7), and based on this synthesis strategy, two routes were developed to achieve the asymmetric synthesis of BDQ by means of the self-designed Li/Li cooperative bimetallic activation strategy (81% yield with 1.4:1 dr and 91% ee; and 22% yield with 16:1 dr, >99% ee, respectively). These BDQ synthesis routes still fail to afford the desired yield, and column chromatography is required in the post-processing process to obtain the product with purity greater than 99%. In addition, due to the limitation of the traditional batch reaction process, this BDQ synthesis route struggles with long reaction time, cumbersome operation, and introduction of impurities, and there is also a great safety hazard because of the introduction of the active butyl lithium reagent.

In summary, the existing BDQ synthesis techniques still have technical defects such as low yield, long production period, high cost, complicated operation, and low safety. Therefore, it is of great research significance and application value to develop a new synthetic technique for BDQ.

SUMMARY

To solve the technical defects in the existing preparation of bedaquiline (BDQ), such as low yield, long production period, complicated operation, and low safety, this application provides a low-temperature continuous-flow method for preparing BDQ, which has excellent yield, simple synthesis and purification operation, high safety, desirable purity (99.8% or more) and short production cycle.

This application provides a continuous-flow preparation method BDQ, comprising:
  (a) subjecting a first feed liquid and a second feed liquid to a first continuous flow reaction for 30-600 seconds to obtain a first reaction mixture;
  wherein the first feed liquid is a mixture of (1S,2R)-2-amino-1, 2-diphenylethanol, N-methylpiperazine, butyllithium, lithium chloride, and tetrahydrofuran; and the second feed liquid is a mixture of 6-bromo-3-benzyl-2-methoxyquinoline and tetrahydrofuran;
  (b) subjecting the first reaction mixture and a third feed liquid to a second continuous flow reaction for 30-600 seconds to obtain a second reaction mixture; wherein the third feed liquid is a mixture of 3-dimethylamino-1-naphthyl-1-acetone and tetrahydrofuran; and
  (c) quenching the second reaction mixture.

In an embodiment, at least one of the first continuous flow reaction and the second continuous flow reaction is carried out in a continuous flow reactor. Preferably, the continuous flow reactor is a reaction tube.

In an embodiment, the first continuous flow reaction is carried out for 30 s-90 s or 180 s-600 s, for example, 300 s, 360 s, 240 s, 600 s or 180 s. The first continuous flow reaction comprises an acid-base reaction and an allotropic reaction between the first feed liquid and the second feed liquid.

In an embodiment, the second continuous flow reaction is carried out for 30 s-60 s or 120 s-360 s; for example, 180 s, 300 s, 120 s, 144 s, or 360 s.

In an embodiment, a reaction temperature of the first continuous flow reaction may be −80° C. to 0° C., preferably −80° C. to −10° C., more preferably −30° C. to −20° C., such as −20° C. or −30° C.

In an embodiment, a reaction temperature of the second continuous flow reaction may be −80° C. to 0° C., preferably −80° C. to −20° C., more preferably −80° C. to −50° C., such as −50° C., −60° C., −70° C., or −80° C.

In an embodiment, in step (a), a flow rate of the first feed liquid is 10 to 500 mL/min, preferably 10 to 200 mL/min, and more preferably 10 to 40 mL/min, for example, 10 mL/min, 12 mL/min, 15 mL/min, 20 mL/min or 30 mL/min.

In an embodiment, in step (a), a flow rate of the second feed liquid is 10 to 500 mL/min, preferably 10 to 200 mL/min, and more preferably 10 to 40 mL/min, for example 10 mL/min, 12 mL/min, 15 mL/min, 20 mL/min or 30 mL/min.

In an embodiment, in step (b), a flow rate of the third feed liquid is 10 to 500 mL/min, preferably 10 to 200 mL/min, and more preferably 10 to 40 mL/min, for example 10 mL/min, 12 mL/min, 15 mL/min, 20 mL/min or 30 mL/min.

In step (b), it is known to the person skilled in the art that a flow rate of the first reaction mixture may be determined after the first feed liquid and second feed liquid have entered the apparatus employing a continuous flow reaction, such as a microchannel. In an embodiment, the flow rate of the first reaction mixture may be 10 to 500 mL/min, preferably 10-40 mL/min, such as 10 mL/min, 12 mL/min, 15 mL/min, 20 mL/min or 30 mL/min.

In an embodiment, in step (a), a ratio of the number of moles of (1S,2R)-2-amino-1, 2-diphenylethanol to a volume of tetrahydrofuran in the first feed liquid is preferably 0.1-0.7 mol/L; for example, 0.298 mol/L, 0.26 mol/L, 0.51 mol/L, 0.1428 mol/L, or 0.28 mol/L.

In an embodiment, in step (a), a ratio of the number of moles of N-methylpiperazine to the volume of tetrahydrofuran in the first feed liquid is preferably 0.1 mol/L-0.7 mol/L, for example, 0.355 mol/L, 0.312 mol/L, 0.170 mol/L, 0.609 mol/L, 0.1704 mol/L, 0.359 mol/L, or 0.284 mol/L.

In an embodiment, in step (a), a ratio of the number of moles of lithium chloride to the volume of tetrahydrofuran in the first feed liquid is preferably 0.1-0.8 mol/L, for example, 0.408 mol/L, 0.354 mol/L, 0.7 mol/L, 0.196 mol/L, or 0.338 mol/L.

In an embodiment, in step (a), a ratio of the number of moles of butyllithium to the volume of tetrahydrofuran in the first feed liquid is 0.4-1.2 mol/L, for example, 0.56 mol/L, 0.59 mol/L, 0.66 mol/L, 0.68 mol/L, 0.625 mol/L, 0.543 mol/L, 1.07 mol/L, or 0.3 mol/L.

In an embodiment, in step (a), a ratio of the number of moles of 6-bromo-3-benzyl-2-methoxyquinoline to a volume of tetrahydrofuran in the second feed liquid is 0.04-1.0 mol/L, such as 0.113 mol/L, 0.136 mol/L, 0.17 mol/L, or 0.057 mol/L.

In an embodiment, in step (a), a ratio of the number of moles of 3-dimethylamino-1-naphthyl-1-acetone to a volume of tetrahydrofuran in the third feed liquid is 0.04-1.0 mol/L, for example 0.115 mol/L, 0.141 mol/L, 0.152 mol/L, 0.630 mol/L, 0.136 mol/L, 0.163 mol/L, or 0.255 mol/L.

In an embodiment, in step (a), a molar ratio of N-methylpiperazine and 6-bromo-3-benzyl-2-methoxyquinoline is 0.5-5.0:1, preferably 1.5-5.0:1, for example, 4.5:1, 2.5:1, 2.1:1, 2:1.

In an embodiment, in step (a), a molar ratio of (1S,2R)-2-amino-1, 2-diphenylethanol to 6-bromo-3-benzyl-2-methoxyquinoline is 0.8-5.0:1, preferably 1.5-5.0:1, for example, 3.0:1, 2.1:1, 1.8:1, or 2.0:1.

In an embodiment, in step (a), a molar ratio of lithium chloride to 6-bromo-3-benzyl-2-methoxyquinoline is 0.8-5.0:1, preferably 1.5-5.0:1, for example 2.9:1 or 2.4:1.

In an embodiment, in step (a), a molar ratio of butyllithium to 6-bromo-3-benzyl-2-methoxyquinoline is 1.0-10.0:1, preferably 3.0-10.0:1, for example, 3.68:1 or 4.41:1.

In an embodiment, in step (a), a molar ratio of 3-dimethylamino-1-naphthyl-1-propanone to 6-bromo-3-benzyl-2-methoxyquinoline is 0.8-5.0:1, preferably 1.5-5.0:1, for example, 1.1:1, 1.2:1, 1.3:1, 1.5:1, or 2.5:1.

In an embodiment, in step (a), a mixture of (1S,2R)-2-amino-1, 2-diphenylethanol, N-methylpiperazine, butyllithium, lithium chloride, and tetrahydrofuran can be obtained by a method conventional in the art, for example, by mixing and reacting (1S,2R)-2-amino-1, 2-diphenylethanol, N-methylpiperazine, butyllithium, lithium chloride and tetrahydrofuran.

In an embodiment, the first reaction mixture is obtained at −80° C. to 0° C., preferably −80° C. to −10° C., more preferably −30° C. to −20° C., for example, −20° C. and −30° C. The reaction time is 10 min-2 h, preferably 20-30 min, for example 20 min and 30 min.

It is known to those skilled in the art that tetrahydrofuran is used as a solvent in the reaction.

In an embodiment, in step (a), the temperature of the first reaction mixture is preferably −80° C. to 0° C., better −80° C. to −10° C., especially −30° C. to −20° C.; for example −20° C. and −30° C.

In an embodiment, in step (a), the mixture of 6-bromo-3-benzyl-2-methoxyquinoline and tetrahydrofuran can be obtained by a conventional method in the art, for example, by mixing 6-bromo-3-benzyl-2-methoxyquinoline and tetrahydrofuran.

In an embodiment, in step (b), the mixture of 3-dimethylamino-1-naphthyl-1-acetone and tetrahydrofuran can be obtained by a conventional method in the art, for example, by mixing 3-dimethylamino-1-naphthyl-1-acetone and tetrahydrofuran.

In an embodiment, the quenching can be performed by two ways.

In a first way, in step (c), the second reaction mixture is quenched with a quenching reagent in a quenching device, and the quenching device is not a continuous flow reactor in which the first continuous flow reaction and the second continuous flow reaction are carried out; the quenching reagent may be a conventional quenching solvent in the art, preferably an ammonium chloride solution.

In a second way, the second reaction mixture obtained in step (b) and a fourth feed liquid are subjected to a continuous quenching reaction; wherein the fourth feed liquid is a quenching solvent. In an embodiment, the quenching solvent is a protic solvent selected from the group consisting of methanol, ethanol and a combination thereof. A flow rate of the fourth feed liquid may be 10-500 mL/min, preferably 10-200 mL/min, more preferably 10-40 mL/min, such as 10 mL/min, 12 mL/min, 15 mL/min, 20 mL/min or 30 mL/min. The continuous quenching reaction may be carried out in the continuous flow reactor. In an embodiment, the continuous flow reactor is a reaction tube.

In an embodiment, after the step (c), the continuous-flow preparation method further comprises a post-treatment comprising extraction, recrystallisation and pulping.

In an embodiment, a recrystallisation solvent and a pulping solvent may be recrystallisation solvents and pulping solvents conventional in the art, preferably independently selected from the group consisting of toluene, ethyl acetate, hexane, ethanol, isopropanol, benzene, isopropyl ether, and a combination thereof. The ethanol is preferably anhydrous ethanol.

In an embodiment, the recrystallisation is performed through the steps of removing an extraction solvent to obtain a filtrate; and preparing a saturated solution of the filtrate with the recrystallisation solvent following by crystallization to obtain the diastereoisomer of BDQ.

The extraction solvent is removed through steps of: subjecting an organic phase collected after the extraction to rotary evaporation until a solid is precipitated, and filtration to obtain the filtrate.

The "crystallization" is performed through steps of: cooling the saturated solution to form a supersaturated solution to allow precipitation of crystals followed by filtering and rotary evaporation to remove the recrystallisation solvent. The cooling temperature is −20-0° C., preferably −20 to −15° C. After the rotary evaporation, the pure BDQ product is obtained by pulping.

It is known to the person skilled in the art that for obtaining a pure BDQ product, the pulping is generally followed by filtration.

In an embodiment, the filtration may be a conventional method in the art, such as suction filtration.

This application also provides a product prepared by the continuous-flow preparation method of BDQ as described above.

In an embodiment, a reaction formula for preparing BDQ as described is as follows:

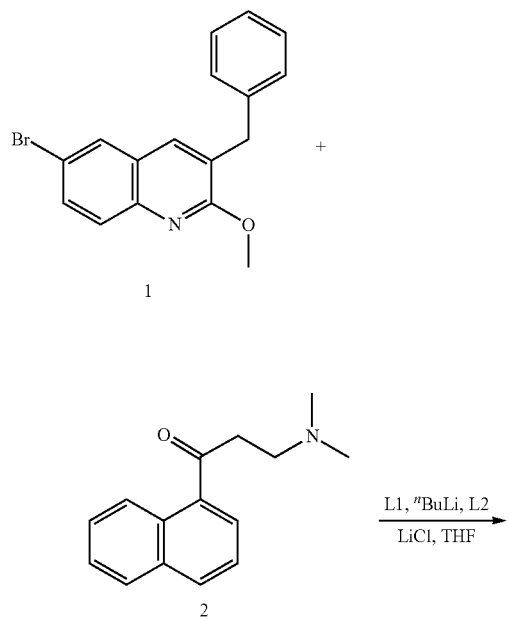

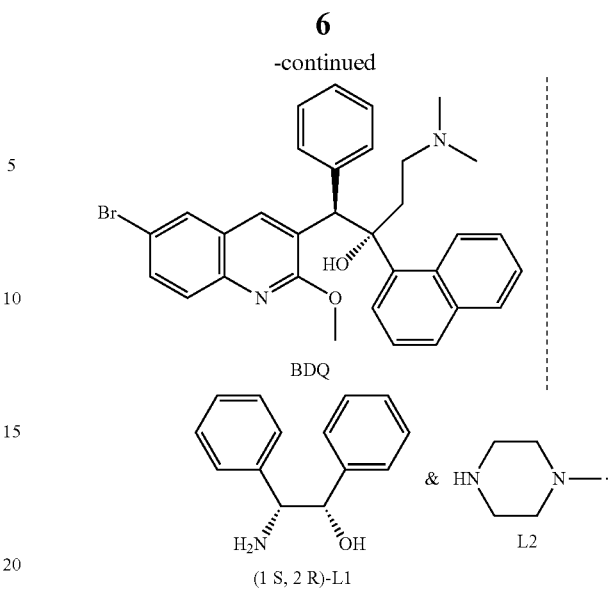

It has been found that if 6-bromo-3-benzyl-2-methoxyquinoline was dissolved together into the first feed liquid and then mixed with the second feed liquid to react, it would not cause too much effect in terms of the reaction mechanism, but since the fluid viscosity of the reaction phase may increase due to the large amount of material, which would ultimately block the continuous flow pipeline, resulting in damage to the equipment and the reaction unable to be carried out.

As is known in the art, the above preferred conditions can be arbitrarily combined to obtain better examples.

The reagents and raw materials used in this application are commercially available.

Compared to the prior art, this application has the following beneficial effects.

This application prepares BDQ by using the whole reaction phase of the first feed liquid as a catalyst and combining the cost-effective and high-efficiency asymmetric synthetic strategy with the continuous flow technology, thereby avoiding the problems of difficult temperature control, and time-consuming dropwise addition and stirring process in the traditional batch synthesis, shortening the production cycle, eliminating the safety hazardous caused by the active lithium reagent, and improving the yield. Moreover, only a simple post-processing operation is required to give the high-purity BDQ (99.8% or more) from the quenched reaction mixture, which reduces the cost, and is suitable for industrial production.

In the case of feeding 100 g of raw materials, to reach the same yield or purity, this application only requires 3 hours, and by comparison, the asymmetric synthesis route A previously disclosed by the team of Prof. Zhang Wanbin from Shanghai Jiaotong University (Sci. China Chem. 2022, 65, 1968-1977) requires 37 hours.

IN THE FIGURES i—continuous flow experimental pump; ii—check valve; iii—pre-cooling tube; iv—reaction tube; v—micro-mixer; $T_1$—temperature at which the feed liquid A and the feed liquid B react; $T_2$—temperature at which a reaction system and the feed liquid C react; $T_3$—quenching temperature; $t_1$—reaction time of the feed liquid A and feed liquid B in the reactor at $T_1$; and $t_2$—reaction time of the reaction mixture D and the feed Liquid C in the reactor at $T_2$.

DETAILED DESCRIPTION OF EMBODIMENTS

The disclosure will be further described below in conjunction with embodiments. The embodiments below facilitate understanding of the disclosure, but do not limit the disclosure. It should be understood that any modifications and variations made by those skilled in the art without departing from the spirit of the disclosure should fall within the scope of the disclosure defined by the appended claims.

In the examples below, it is known to those of ordinary skill in the art that enantiomeric excess (i.e., ee value) is a purity measurement indicator used for chiral substances, which reflects the extent to which the amount of one enantiomer in a sample is higher than that of another. Purity was measured by HPLC on a ChiralpakAD-H chiral column from Daicel Corp, with chromatographically pure isopropanol and n-hexane as mobile phases. dr values were measured by NMR spectrometry (400 MHz or 500 MHz), with the solvent $CDCl_3$. In the following examples, the equivalent for each compound is the molar ratio of the compound to 6-bromo-3-benzyl-2-methoxyquinoline.

Example 1

Figure 1:
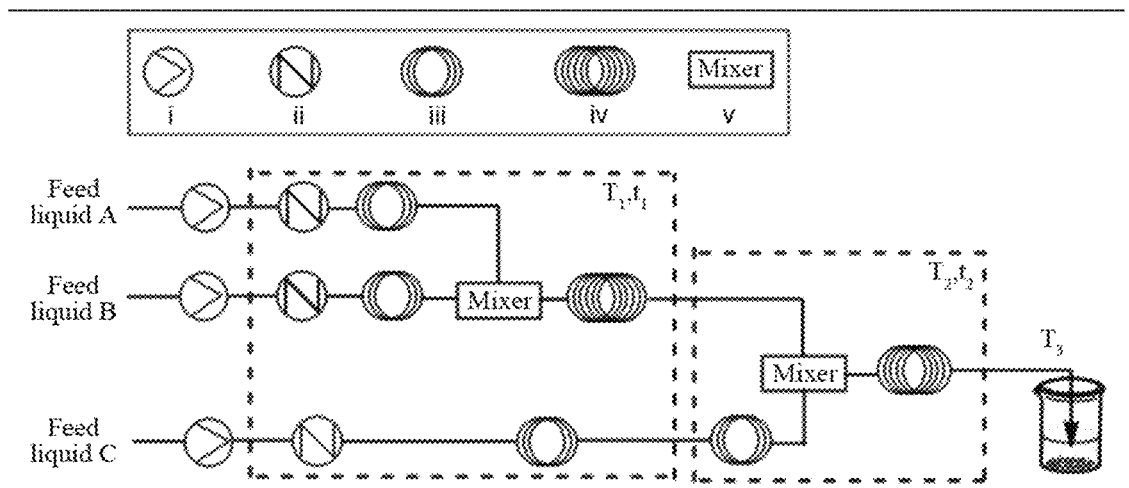
FIG. 1 is a flow chart of a low-temperature continuous-flow preparation method of BDQ in Example 1 of the present disclosure.

Provided herein was a low-temperature continuous-flow preparation of bedaquiline (BDQ), which was shown schematically in FIG. 1.

(S1) To a 5 L dry reactor were added 10.5 g (245 mmol, 2.9 equiv.) of lithium chloride, 38.3 g (178.5 mmol, 2.1 equiv.) of (1S,2R)-2-amino-1, 2-diphenylethanol, 23.9 mL (213 mmol, 2.5 equiv.) of N-methylpiperazine, and 600 mL of anhydrous tetrahydrofuran, and then was added 150 mL of a solution of 2.5 M n-butyllithium (2.5 mol/L, 375 mmol) in n-hexane at −20° C. The mixture was reacted for 30 min to obtain the feed liquid A.

To a 5 L single-necked flask were added 27.9 g (85 mmol) of raw material 1 (i.e., 6-bromo-3-benzyl-2-methoxyquinoline), and 750 mL of anhydrous tetrahydrofuran. The mixture was mixed well to be used as the feed liquid B.

To a 5 L single-necked flask were added 26.9 g (102 mmol) of 3-dimethylamino-1-naphthyl-1-acetone, and 750 mL of anhydrous tetrahydrofuran. The mixture was mixed well and used as the feed liquid C.

In this example, the flow rate of the feed liquid A was 15 mL/min, the flow rate of the feed liquid B was 15 mL/min, and the flow rate of the feed liquid C was 15 mL/min.

(S2) The feed liquid A and the feed liquid B were pumped into a first microreactor tube for a first continuous flow reaction at $T_1$=−20° C. for $t_1$=5 min to obtain a reaction mixture D.

(S3) The reaction mixture D and the feed liquid C were pumped into a second microreactor tube for a second continuous flow reaction at $T_2$=−60° C. for $t_2$=3 min.

(S4) The reaction mixture flowing out from the second microreactor tube was quenched with 2 L of a saturated ammonium chloride solution at $T_3$=−60° C. The quenched reaction mixture was collected, in which BDQ was contained.

(S5) Post-treatment: extraction, recrystallisation and pulping

Extraction: the reaction mixture obtained from step (S4) was subjected to extraction with ethyl acetate 3 times each for 1 L in a 5 L reactor, and an organic phase was collected as the crude product.

Recrystallisation: the extraction solvent was removed to obtain a filtrate, and a saturated solution of the filtrate was prepared with the recrystallisation solvent, and crystallized.

Specifically, the organic phase is subjected to rotary evaporation to remove the extraction solvent and allow the precipitation of a solid, and filtered to obtain the filtrate. The saturated solution of the filtrate was cooled at −20° C. to −15° C. to form the supersaturated solution to allow crystal precipitation, and filtered to obtain the filtrate, which was then treated by rotary evaporation.

Specifically, the organic phase was subjected to rotary evaporation on the rotary evaporator until the solid appeared, let to stand overnight to precipitate the first solid, and subjected to vacuum filtration to obtain the filtrate. The filter cake was rinsed with n-hexane, and the filtrate cake was mostly composed of diastereomers and ligands. The filtrate was added with n-hexane in an amount equal to the organic solvent, cooled to allow the precipitation of crystals from the supersaturated solution, filtered under vacuum until most of the filtrate was the target product, and the filtrate was subjected to rotary evaporation to obtain the second solid.

Pulping: the second solid was mixed with ethanol, pulped at room temperature for 12 h, and filtered under vacuum, and the filter cake was collected, washed with n-hexane, and dried under vacuum at room temperature to obtain the pure BDQ.

The crude product was analyzed by Nuclear Magnetic Resonance (NMR) spectroscopy and HPLC. The NMR results showed that the dr value and yield of BDQ in the crude product were 1:1 and 95%, respectively, and the HPLC results showed that the ee value of BDQ was 60%. The yield was calculated as follows: triphenylmethane was used as the internal standard; the formula was as follows: an integral of the characteristic peak of the internal standard was set as 1; yield=x*y/n, where x=the integral of the characteristic peak of the target product; y=the number of moles of the internal standard; and n=the number of moles of the raw material 1.

The pure BDQ obtained was a white solid; as demonstrated by HPLC, the purity of the pure product was >99.8%, and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Example 2

Figure 2:
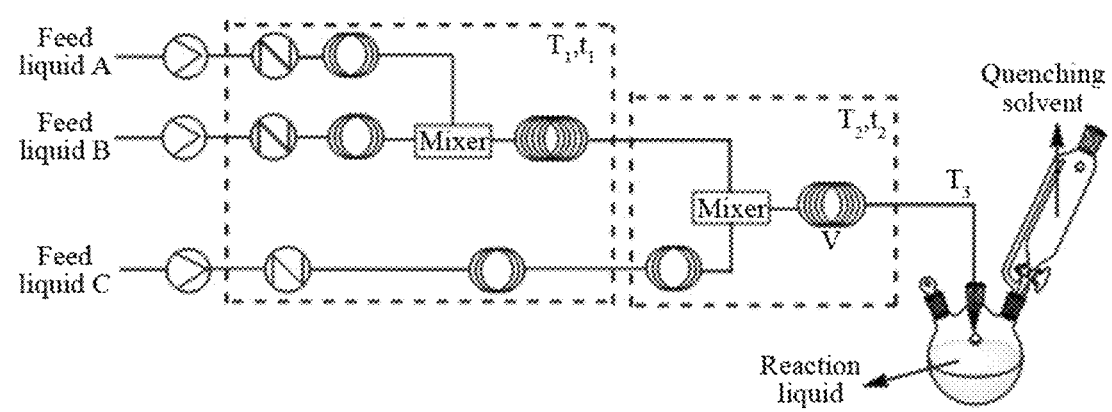
FIG. 2 is a flow chart of a low-temperature continuous-flow preparation method of BDQ in Example 2 of the present disclosure.

Provided herein was a low-temperature continuous-flow preparation of bedaquiline (BDQ), which was shown schematically in FIG. 2.

(S1) To a 5 L dry reactor were added 10.5 g (245 mmol, 2.9 equiv.) of lithium chloride, 38.3 g (178.5 mmol, 2.1 equiv.) of (1S,2R)-2-amino-1, 2-diphenylethanol, 23.9 mL (213 mmol, 2.5 equiv.) of N-methylpiperazine, and 600 mL of anhydrous tetrahydrofuran, and then was added 150 mL of a solution of 2.5 M (2.5 mol/L, 375 mmol) n-butyllithium in n-hexane at −20° C. The mixture was reacted for 30 min to obtain the feed liquid A.

To a 5 L single-necked flask were added 27.9 g (85 mmol) of raw material 1 (i.e., 6-bromo-3-benzyl-2-methoxyquinoline), and 750 mL of anhydrous tetrahydrofuran. The mixture was mixed well to be used as the feed liquid B.

To a 5 L single-necked flask were added 26.9 g (102 mmol) of 3-dimethylamino-1-naphthyl-1-acetone (raw material 2), and 750 mL of anhydrous tetrahydrofuran. The mixture was mixed well and used as the feed liquid C.

In this example, the flow rate of the feed liquid A was 15 mL/min, the flow rate of the feed liquid B was 15 mL/min, and the flow rate of the feed liquid C was 15 mL/min.

(S2) The feed liquid A and the feed liquid B were pumped into a first microreactor tube for a first continuous flow reaction at $T_1$=−20° C. for $t_1$=5 min to obtain a reaction mixture D.

(S3) The reaction mixture D and the feed liquid C were pumped into a second microreactor tube for a second continuous flow reaction at $T_2$=−60° C. for $t_2$=3 min.

(S4) The reaction mixture flowing out of the second microreactor tube was quenched with 2 L of a saturated ammonium chloride solution at $T_3$=−60° C. The quenched reaction mixture was collected, in which BDQ was contained.

(S5) Post-treatment: extraction, recrystallisation and pulping

The same extraction method as Example 1 was used to obtain the crude product, and the same steps of recrystallisation and pulping as Example 1 were used to obtain the pure BDQ product.

The crude product was analyzed by NMR spectroscopy and HPLC. Triphenylmethane was used as the internal standard. The NMR results showed that the dr value and yield of BDQ in the crude product were 1:1 and 91%, respectively. The HPLC results showed that the ee value of BDQ was 84%.

As demonstrated by HPLC, the purity of the pure product was >99.8%, and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Example 3

Provided herein was a low-temperature continuous-flow preparation of bedaquiline (BDQ), which was shown schematically in FIG. 2.

(S1) To a 5 L dry reactor were added 10.5 g (245 mmol, 2.9 equiv.) of lithium chloride, 38.3 g (178.5 mmol, 2.1 equiv.) of (1S,2R)-2-amino-1, 2-diphenylethanol, 23.9 mL (213 mmol, 2.5 equiv.) of N-methylpiperazine, and 600 mL of anhydrous tetrahydrofuran, and then was added 150 mL of a solution of 2.5 M (2.5 mol/L, 375 mmol) n-butyllithium in n-hexane at −20° C. The mixture was reacted for 30 min to obtain the feed liquid A.

To a 5 L single-necked flask were added 27.9 g (85 mmol) raw material 1 (i.e., 6-bromo-3-benzyl-2-methoxyquinoline), and 750 mL of anhydrous tetrahydrofuran. The mixture was mixed well to be used as the feed liquid B.

To a 5 L single-necked flask were added 26.9 g (102 mmol) 3-dimethylamino-1-naphthyl-1-acetone (raw material 2), and 750 mL of anhydrous tetrahydrofuran. The mixture was mixed well and used as the feed liquid C.

In this example, the flow rate of the feed liquid A was 20 mL/min, the flow rate of the feed liquid B was 15 mL/min, and the flow rate of the feed liquid C was 15 mL/min.

(S2) The feed liquid A and the feed liquid B were pumped into a first microreactor tube for a first continuous flow reaction at $T_1$=−20° C. for $t_1$=5 min to obtain a reaction mixture D.

(S3) The reaction mixture D and the feed liquid C were pumped into a second microreactor tube for a second continuous flow reaction at $T_2$=−60° C. for $t_2$=3 min.

(S4) The reaction mixture flowing out of the second microreactor tube was quenched with 2 L of a saturated ammonium chloride solution at $T_3$=−60° C. The quenched reaction mixture was collected, in which BDQ was contained.

(S5) Post-treatment: extraction, recrystallisation and pulping

The same extraction method as Example 1 was used to obtain the crude product, and the same steps of recrystallisation and pulping as Example 1 were used to obtain the pure BDQ product.

The crude product was analyzed by NMR spectroscopy and HPLC. Triphenylmethane was used as the internal standard. The NMR results showed that the dr value and yield of BDQ in the crude product were 1:1 and 91%, respectively. The HPLC results showed that the ee value of BDQ was 90%.

As demonstrated by HPLC, the purity in the pure product was >99.8%, and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Example 4

Provided herein was a low-temperature continuous-flow preparation of bedaquiline (BDQ), which was shown schematically in FIG. 1.

(S1) To a 5 L dry reactor were added 20.8 g (490 mmol, 2.9 equiv.) of lithium chloride, 76.6 g (359 mmol, 2.1 equiv.) of (1S,2R)-2-amino-1, 2-diphenylethanol, 47.8 mL (431 mmol, 2.5 equiv.) of N-methylpiperazine, and 1.2 L of anhydrous tetrahydrofuran, and then was added 300 mL of a solution of 2.5 M (2.5 mol/L, 750 mmol) n-butyllithium in n-hexane at −20° C. The mixture was reacted for 30 min to obtain the feed liquid A.

To a 5 L single-necked flask were added 55.8 g (170 mmol) of raw material 1, and 1.5 L of anhydrous tetrahydrofuran. The mixture was mixed well to be used as the feed liquid B.

To a 5 L single-necked flask were added 60 g (227.5 mmol) of 3-dimethylamino-1-naphthyl-1-acetone, and 1.5 L of anhydrous tetrahydrofuran. The mixture was mixed well and used as the feed liquid C.

In this example, the flow rate of the feed liquid A was 15 mL/min, the flow rate of the feed liquid B was 15 mL/min, and the flow rate of the feed liquid C was 15 mL/min.

(S2) The feed liquid A and the feed liquid B were pumped into a first microreactor tube for a first continuous flow reaction at $T_1=-20°$ C. for $t_1=5$ min to obtain a reaction mixture D.

(S3) The reaction mixture D and the feed liquid C were pumped into a second microreactor tube for a second continuous flow reaction at $T_2=-60°$ C. for $t_2=3$ min.

(S4) The reaction mixture flowing out of the second microreactor tube was quenched with 2 L of a saturated ammonium chloride solution at $T_3=0°$ C. The quenched reaction mixture was collected, in which BDQ was contained.

(S5) Post-treatment: extraction, recrystallisation and pulping

The same extraction steps as Example 1 were used to obtain the crude product, and the same steps of recrystallisation and pulping as Example 1 were used to obtain the pure product.

The crude product was analyzed by NMR spectroscopy and HPLC. Triphenylmethane was used as the internal standard. The NMR results showed that the dr value and yield of BDQ in the crude product were 1:1 and 93%, respectively. The HPLC results showed that the ee value of BDQ was 86%.

As demonstrated by HPLC, the purity of the pure product was >99.8%, and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Example 5

Provided herein was a low-temperature continuous-flow preparation of bedaquiline (BDQ), which was shown schematically in FIG. 1.

(S1) To a 5 L dry reactor were added 34.6 g (816 mmol, 2.4 equiv.) of lithium chloride, 127.5 g (598 mmol, 1.8 equiv.) of (1S,2R)-2-amino-1, 2-diphenylethanol, 79.5 mL (717 mmol, 2.1 equiv.) of N-methylpiperazine, and 2.3 L of anhydrous tetrahydrofuran, and then was added 500 mL of a solution of 2.5 M (2.5 mol/L, 1250 mmol) n-butyllithium in n-hexane at −20° C. The mixture was reacted for 30 min to obtain the feed liquid A.

To a 5 L single-necked flask were added 111.6 g (340 mmol) of raw material 1, and 2.5 L of anhydrous tetrahydrofuran. The mixture was mixed well to be used as the feed liquid B.

To a 5 L single-necked flask were added 104 g (408 mmol) of 3-dimethylamino-1-naphthyl-1-acetone (raw material 2), and 2.5 L of anhydrous tetrahydrofuran. The mixture was mixed well and used as the feed liquid C.

In this example, the flow rate of the feed liquid A was 15 mL/min, the flow rate of the feed liquid B was 15 mL/min, and the flow rate of the feed liquid C was 15 mL/min.

(S2) The feed liquid A and the feed liquid B were pumped into a first microreactor tube for a first continuous flow reaction at $T_1=-20°$ C. for $t_1=5$ min to obtain reaction mixture D.

(S3) The reaction mixture D and the feed liquid C were pumped into a second microreactor tube for a second continuous flow reaction at $T_2=-60°$ C. for $t_2=3$ min.

(S4) The reaction mixture flowing out of the second microreactor tube was quenched with 2 L of saturated ammonium chloride solution at $T_3=0°$ C. The quenched reaction mixture was collected, in which BDQ was contained.

(S5) Post-treatment: extraction, recrystallisation and pulping

The same extraction steps as Example 1 were used to obtain the crude product, and the same steps of recrystallisation and pulping as Example 1 were used to obtain the pure BDQ product.

The crude product was analyzed by NMR spectroscopy and HPLC. Triphenylmethane was used as the internal standard. The NMR results showed that the dr value and yield of BDQ in the crude product were 1.2:1 and 89%, respectively. The HPLC results showed that the ee value of BDQ was 63%.

As demonstrated by HPLC, the purity of the pure product was >99.8%, and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Example 6

Figure 3:
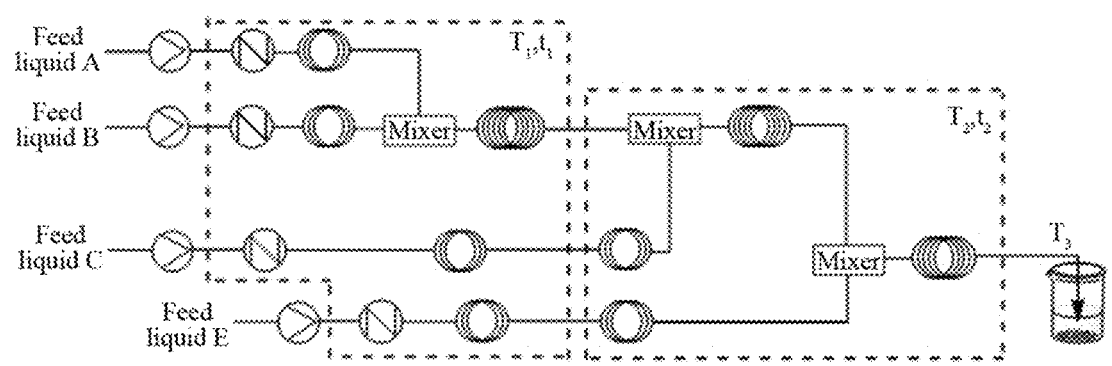
FIG. 3 is a flow chart of a low-temperature continuous-flow preparation method of BDQ in Example 6 of the present disclosure.

Provided herein was a low-temperature continuous-flow preparation of bedaquiline (BDQ), which was shown schematically in FIG. 3.

(S1) To a 5 L dry reactor were added 34.6 g (816 mmol, 2.4 equiv.) of lithium chloride, 127.5 g (598 mmol, 1.8 equiv.) of (1S,2R)-2-amino-1, 2-diphenylethanol, 79.5 mL (717 mmol, 2.1 equiv.) of N-methylpiperazine, and 2.3 L of anhydrous tetrahydrofuran, and then was added 500 mL of a solution of 2.5 M (2.5 mol/L, 1250 mmol) n-butyllithium in n-hexane at −20° C. The mixture was reacted for 30 min to obtain the feed liquid A.

To a 5 L single-necked flask were added 111.6 g (340 mmol) of raw material 1, and 2.5 L of anhydrous tetrahydrofuran. The mixture was mixed well to be used as the feed liquid B.

To a 5 L single-necked flask were added 104 g (408 mmol) of 3-dimethylamino-1-naphthyl-1-acetone (raw material 2), and 2.5 L of anhydrous tetrahydrofuran. The mixture was mixed well and used as the feed liquid C.

In this example, the flow rate of the feed liquid A was 15 mL/min, the flow rate of the feed liquid B was 15 mL/min, and the flow rate of the feed liquid C was 15 mL/min.

(S2) The feed liquid A and the feed liquid B were pumped into a first microreactor tube for a first continuous flow reaction at $T_1=-20°$ C. for $t_1=5$ min to obtain a reaction mixture D.

(S3) The reaction mixture D and the feed liquid C were pumped into a second microreactor tube for a second continuous flow reaction at $T_2=-60°$ C. for $t_2=3$ min.

(S4) 1 L of anhydrous ethanol was added into a 5 L single-necked flask as a feed liquid E. The reaction solution obtained from step (S3) and the feed liquid E were added to a third microreactor tube for a continuous quenching reaction, in which the flow rate of the feed liquid E was 10 mL/min; the temperature of quenching was 0° C. The quenched reaction mixture was collected, in which BDQ was contained.

(S5) Post-treatment: extraction, recrystallisation and pulping

The same extraction steps as Example 1 were used to obtain the crude product, and the same steps of recrystallisation and pulping as Example 1 were used to obtain the pure BDQ product.

The crude product was analyzed by NMR spectroscopy and HPLC. Triphenylmethane was used as the internal standard. The NMR results showed that the dr value and yield of BDQ in the crude product were 1.2:1 and 92%, respectively. The HPLC results showed that the ee value of BDQ was 68%.

As demonstrated by HPLC, the purity of the pure product was >99.8%, and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Example 7

Example 7 differed from Example 1 only in that the reaction temperature $T_1$ for the first continuous flow reaction was $-30°$ C., and $T_2$ for the second continuous flow reaction was $-70°$ C. The rest of the steps were the same.

The crude product was analyzed by Nuclear Magnetic Resonance (NMR) spectroscopy and HPLC. The NMR results showed that the dr value and yield of BDQ in the crude product were 1:1 and 91%, respectively. The HPLC results showed that the ee value of BDQ was 78%. Triphenylmethane was used as the internal standard.

As demonstrated by HPLC, the purity of the pure product was >99.8%, and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Example 8

Example 8 differed from Example 7 only in that the reaction temperature $T_2$ for the second continuous flow reaction was $-80°$ C. The rest of the steps were the same.

The crude product was analyzed by NMR spectroscopy and HPLC. Triphenylmethane was used as the internal standard. The NMR results showed that the dr value and yield of BDQ in the crude product were 1:1 and 91%, respectively. The HPLC results showed that the ee value of BDQ was 78%.

As demonstrated by HPLC, the purity of the pure product was >99.8%, and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Example 9

Example 9 differed from Example 2 only in that the reaction temperature $T_2$ of the second continuous flow reaction was $-70°$ C. The rest of the steps were the same.

The crude product was analyzed by NMR spectroscopy and HPLC. Triphenylmethane was used as the internal standard. The NMR results showed that the dr value and yield of BDQ in the crude product were 1:1 and 92%, respectively. The HPLC results showed that the ee value of BDQ was 88%.

As demonstrated by HPLC, the purity of the pure product was >99.8%, and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Example 10

Example 10 differed from Example 2 only in that the flow rate of the feed liquid A was 10 mL/min, the flow rate of the feed liquid B was 10 mL/min, the flow rate of the feed liquid C was 10 mL/min; the reaction time of the first continuous flow reaction was $t_1=6$ min, and the reaction time of the second continuous flow reaction was $t_2=5$ min; and the temperature of quenching was $-60°$ C. The rest of the steps were the same.

The crude product was analyzed by NMR spectroscopy and HPLC. Triphenylmethane was used as the internal standard. The NMR results showed that the dr value and yield of BDQ in the crude product were 1:1 and 91%, respectively. The HPLC results showed that the ee value of BDQ was 84%.

As demonstrated by HPLC, the purity of the pure product was >99.8%, and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Example 11

Example 11 differed from Example 2 only in that step (S1) was different, and the temperature of quenching in step (S4) was different. The rest of the steps were the same.

(S1) To a 5 L dry reactor were added 8.7 g (203 mmol, 2.4 equiv.) of lithium chloride, 36.3 g (170 mmol, 2.0 equiv.) of (1S,2R)-2-amino-1, 2-diphenylethanol, 23.9 mL (170.4 mmol, 2 equiv.) of N-methylpiperazine, and 600 mL anhydrous tetrahydrofuran, and then was added 150 mL of a solution of 2.5 M (2.5 mol/L, 375 mmol) n-butyllithium in n-hexane at −20° C. The mixture was reacted for 20 min to obtain the feed liquid A.

To a 5 L single-necked flask were added 27.9 g (85 mmol) raw material 1, and 750 mL of anhydrous tetrahydrofuran. The mixture was mixed well to be used as the feed liquid B.

To a 5 L single-necked flask were added 26.9 g (102 mmol) of 3-dimethylamino-1-naphthyl-1-acetone (raw material 2), and 750 mL of anhydrous tetrahydrofuran. The mixture was mixed well and used as the feed liquid C.

In this example, the flow rate of the feed liquid A was 15 mL/min, the flow rate of the feed liquid B was 15 mL/min, and the flow rate of the feed liquid C was 15 mL/min.

The temperature $T_3$ of quenching in step (S4) was −78° C.

The crude product was analyzed by NMR spectroscopy and HPLC. Triphenylmethane was used as the internal standard. The NMR results showed that the dr value and yield of BDQ in the crude product were 1:1 and 88%, respectively. The HPLC results showed that the ee value of BDQ was 80%.

As demonstrated by HPLC, the purity of the pure product was >99.8%; and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Example 12

Example 12 differed from Example 2 only in that the volume of tetrahydrofuran used in step (S1) was different, and the reaction time was different, and the temperature of quenching in step S4 was different. The rest of the steps were the same.

(S1) To a 5 L dry reactor were added 10.5 g (245 mmol, 2.9 equiv.) of lithium chloride, 38.3 g (178.5 mmol, 2.1 equiv.) of (1S,2R)-2-amino-1, 2-diphenylethanol, 23.9 mL (213 mmol, 2.5 equiv.) of N-methylpiperazine, and 350 mL anhydrous tetrahydrofuran, and then was added 150 mL of a solution of 2.5 M (2.5 mol/L, 375 mmol) n-butyllithium in n-hexane at −20° C. The mixture was reacted for 30 min to obtain the feed liquid A.

To a 5 L single-necked flask were added 27.9 g (85 mmol) raw material 1, and 500 mL of anhydrous tetrahydrofuran. The mixture was mixed well to be used as the feed liquid B.

To a 5 L single-necked flask were added 28.9 g (127.5 mmol) 3-dimethylamino-1-naphthyl-1-acetone (raw material 2), and 500 mL of anhydrous tetrahydrofuran. The mixture was mixed well and used as the feed liquid C.

In this example, the flow rate of the feed liquid A was 15 mL/min, the flow rate of the feed liquid B was 15 mL/min.

The reaction time $t_1$ for the first continuous flow reaction in step (S2) was 4 min.

The reaction time $t_2$ of the second continuous flow reaction in step (S3) was 2 min.

The temperature $T_3$ of quenching in step (S4) was −78° C.

The crude product was analyzed by NMR spectroscopy and HPLC. Triphenylmethane was used as the internal standard. The NMR results showed that the dr value and yield of BDQ in the crude product were 1:1 and 86%, respectively. The HPLC results showed that the ee value of BDQ was 76%.

As demonstrated by HPLC, the purity of the pure product was >99.8%; and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Compared Example 12 with Example 2, the amount of anhydrous tetrahydrofuran in each reaction phase was less, therefore the concentration of the material in the reaction process changed, and the retention time in the reactor was shorter, which caused some changes in the reaction results, resulting in lower yields and ee values, but the eventually recrystallized product met the required purity.

Example 13

The differences between Example 13 and Example 2 were only that the volume of tetrahydrofuran used in step (S1) was different, the reaction times in step (S2) and (S3) were different. The rest of the steps were the same.

(S1) To a 5 L dry reactor were added 10.5 g (245 mmol, 2.9 equiv.) of lithium chloride, 38.3 g (178.5 mmol, 2.1 equiv.) of (1S,2R)-2-amino-1, 2-diphenylethanol, 23.9 mL (213 mmol, 2.5 equiv.) of N-methylpiperazine, and 1.25 L of anhydrous tetrahydrofuran, and then was added 150 mL of a solution of 2.5 M (2.5 mol/L, 375 mmol) n-butyllithium in n-hexane at −20° C. The mixture was reacted for 30 min to obtain the feed liquid A.

To a 5 L single-necked flask were added 27.9 g (85 mmol) of raw material 1, and 1.5 L of anhydrous tetrahydrofuran. The mixture was mixed well to be used as the feed liquid B.

To a 5 L single-necked flask were added 26.9 g (102 mmol) of 3-dimethylamino-1-naphthyl-1-acetone (raw material 2), and 1.5 L of anhydrous tetrahydrofuran. The mixture was mixed well and used as the feed liquid C.

In this example, the flow rate of the feed liquid A was 15 mL/min, the flow rate of the feed liquid B was 15 mL/min, and the flow rate of the feed liquid C was 15 mL/min.

The reaction time $t_1$ for the first continuous flow reaction in step (S2) was 10 min.

The reaction time $t_2$ of the second continuous flow reaction in step (S3) was 6 min.

The temperature $T_3$ of quenching in step (S4) was −78° C.

The crude product was analyzed by NMR spectroscopy and HPLC. Triphenylmethane was used as the internal standard. The NMR results showed that the dr value and yield of BDQ in the crude product were 1:1 and 94%, respectively. The HPLC results showed that the ee value of BDQ was 89%.

As demonstrated by HPLC, the purity of the pure product was >99.8%; and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Compared Example 13 with Example 2, the amount of anhydrous tetrahydrofuran in each reaction phase was greater, therefore the concentration of the material in the reaction process changed, and the reaction time was longer, thereby achieving superior yields and ee values.

Example 14

Differences between Example 14 and Example 4 only in that the flow rate of each feed liquid was different, and the reaction time was different. The rest of the steps were the same.

The flow rate of the feed liquid A was 12 mL/min, the flow rate of the feed liquid B was 12 mL/min, and the flow rate of the feed liquid C was 12 mL/min.

The reaction time $t_1$ for the first continuous flow reaction was 4 min, and reaction time $t_2$ for the second continuous flow reaction was 2.4 min.

The crude product was analyzed by NMR spectroscopy and HPLC. Triphenylmethane was used as the internal standard. The NMR results showed that the dr value and yield of BDQ in the crude product were 1:1.2 and 87%, respectively. The HPLC results showed that the ee value of BDQ was 76%.

As demonstrated by HPLC, the purity of the pure product was >99.8%; and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Compared Example 14 to Example 4, the flow rate was lower in each reaction phase, and the reaction time was shorter, so the yield and ee values achieved were lower, and the dr values were lower. The results obtained by changing the flow rates during the reaction were fluctuant but within the error range, and but the final recrystallized product met the required purity.

Example 15

The differences between Example 15 and Example 4 were only that the flow rate of the feed liquid A was 20 mL/min; the flow rate of the feed liquid B is 20 mL/min; the flow rate of the feed liquid C was 20 mL/min; the reaction time $t_1$ of the first continuous-flow reaction was 3 min; and the reaction time $t_2$ of the first continuous-flow reaction was 2 min. The rest of the steps were the same.

The crude product was analyzed by NMR spectroscopy and HPLC. Triphenylmethane was used as the internal standard. The NMR results showed that the dr value and yield of BDQ in the crude product were 1:1 and 90%, respectively. The HPLC results showed that the ee value of BDQ was 81%.

As demonstrated by HPLC, the purity of the pure product was >99.8%; and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Example 16

The differences between Example 16 and Example 4 were only that the reaction temperature $T_1$ for the first continuous flow reaction was −10° C., and the reaction temperature $T_2$ for the second continuous flow reaction was −50° C.

The crude product was analyzed by NMR spectroscopy and HPLC. Triphenylmethane was used as the internal standard. The NMR results showed that the dr value and yield of BDQ in the crude product were 1:1 and 88%, respectively. The HPLC results showed that the ee value of BDQ was 74%.

As demonstrated by HPLC, the purity of the pure product was >99.8%; and the single impurity was <0.1%. The structural characterization data of BDQ was shown as follows.

$^1$HNMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Compared Example 16 with Example 4, both $T_1$ and $T_2$ were higher, but obtained yields and ee values were slightly lower, since the results obtained by changing the temperature conditions during the reaction were fluctuant but within the error range.

Example 17

The differences between Example 17 and Example 4 were only that the reaction temperature $T_1$ for the first continuous flow reaction was −80° C.

The crude product was analyzed by NMR spectroscopy and HPLC. Triphenylmethane was used as the internal standard. The NMR results showed that the dr value and yield of BDQ in the crude product were 1:1 and 88%, respectively. The HPLC results showed that the ee value of BDQ was 72%.

As demonstrated by HPLC, the purity of the pure product was >99.8%, and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Example 18

The differences between Example 18 and Example 2 were only the reaction time $t_1=30$ s for the first continuous flow reaction and the reaction time $t_2=30$ s for the second continuous flow reaction.

The crude product was analyzed by NMR spectroscopy and HPLC. Triphenylmethane was used as the internal standard. The NMR results showed that the dr value and yield of BDQ in the crude product were 1:1 and 89%, respectively. The HPLC results showed that the ee value of BDQ was 83%.

As demonstrated by HPLC, the purity of the pure product was >99.8%, and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Example 19

The difference between Example 19 and Example 2 was only the temperature $T_2=-20°$ C. of the second continuous flow reaction.

The crude product was analyzed by NMR spectroscopy and HPLC. Triphenylmethane was used as the internal standard. The NMR results showed that the dr value and yield of BDQ in the crude product were 1:1 and 87%, respectively. The HPLC results showed that the ee value of BDQ was 85%.

As demonstrated by HPLC, the purity of the pure product was >99.8%, and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Example 20

Example 20 differed from Example 4 only in that the reaction temperature $T_2$ of the second continuous flow reaction was 0° C.

The crude product was analyzed by NMR spectroscopy and HPLC. Triphenylmethane was used as the internal standard. The NMR results showed that the dr value and yield of BDQ in the crude product were 1:1.2 and 60%, respectively. The HPLC results showed that the ee value of BDQ was 59%.

As demonstrated by HPLC, the purity of the pure product was >99.8%, and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Example 21

Example 21 differed from Example 4 only in that the flow rates of the feed liquid A, the feed liquid B and the feed liquid C were all 30 mL/min, which shortened the reaction time of the reaction solution, and the reaction time for the first continuous flow reaction was $t_1=2$ min; and the reaction time for the second continuous flow reaction was $t_2=1.5$ min.

The crude product was analyzed by NMR spectroscopy and HPLC. Triphenylmethane was used as the internal standard. The NMR results showed that the dr value and yield of BDQ in the crude product were 1:1.4 and 68%, respectively. The HPLC results showed that the ee value of BDQ was 60%.

As demonstrated by HPLC, the purity of BDQ in the pure product was >99.8%, and the single impurity was <0.1%. The structural characterization data of BDQ was shown as follows.

$^1$H NMR (400 MHz, CDCl$_3$): δ8.89 (s, 1H), 8.60 (d, J=8.8 Hz, 1H), 7.96 (d, J=2.0 Hz, 1H), 7.90 (d, J=7.2 Hz, 1H), 7.87 (d, J=8.4 Hz, 1H), 7.71 (d, J=8.8 Hz, 1H), 7.66-7.59 (m, 3H), 7.51-7.46 (m, 1H), 7.30 (t, J=8.0 Hz, 1H), 7.16-7.12 (m, 2H), 6.88-6.87 (m, 3H), 5.89 (s, 1H), 4.21 (s, 3H), 2.54-2.50 (m, 1H), 2.13-2.00 (m, 2H), 1.97 (s, 6H), 1.95-1.90 (m, 1H).

Experimental Example 1

The enantiomeric excess percentage test (i.e., ee value) of BDQ was conducted on the crude products obtained from Examples 1-21.

Chromatographic Conditions:

The chromatographic column was a ChiralpakAD-H chiral column from Daicel Corp, Japan. The HPLC Instrument was LC-2010 from Shimadzu Corporation.

Mobile phase: chromatographically pure isopropanol and n-hexane

Flow rate: 0.5 mL/min

Hexane/i-PrOH=98/2 (the volume ratio of hexane to isopropanol)

Detection wavelength: 220 nm

Figure 4:
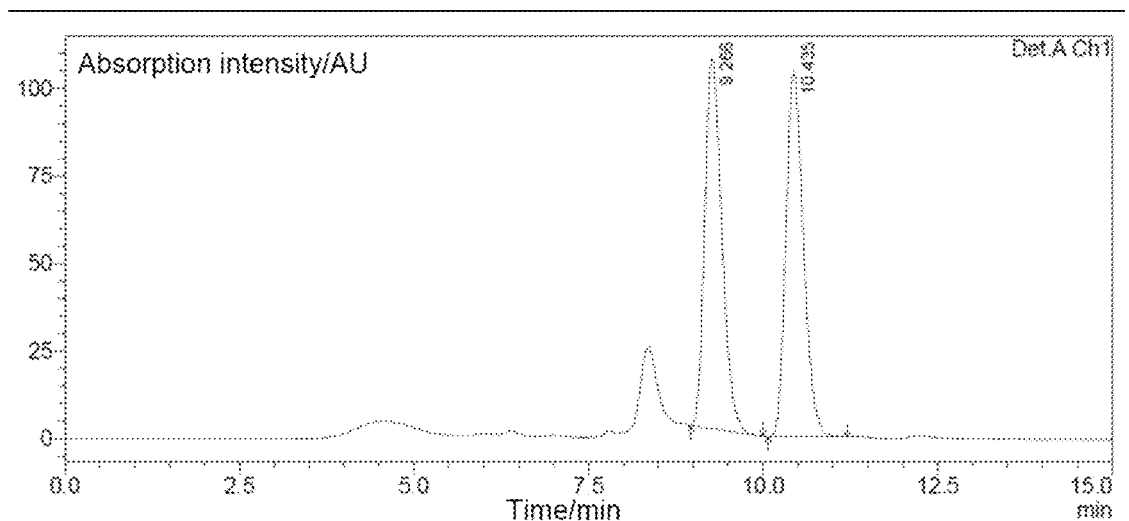
FIG. 4 is a High-Performance Liquid Chromatography (HPLC) graph of BDQ racemate prepared in Example 1 of the present disclosure.

FIG. 4 was the HPLC graph of BDQ racemate, which was required for the determination of the ee value of BDQ. The peak area and retention time of the racemate were shown in Table 1 below.

TABLE 1

Peak area and retention time data of BDQ racemate

| Peak No. | Retention time | Area | Height | Area % | Height % |
|---|---|---|---|---|---|
| 1 | 9.266 | 1809937 | 105980 | 49.790 | 50.368 |
| 2 | 10.435 | 1825213 | 104432 | 50.210 | 49.632 |
| Total | | 3635150 | 210412 | 100.000 | 100.000 |

Figure 5:
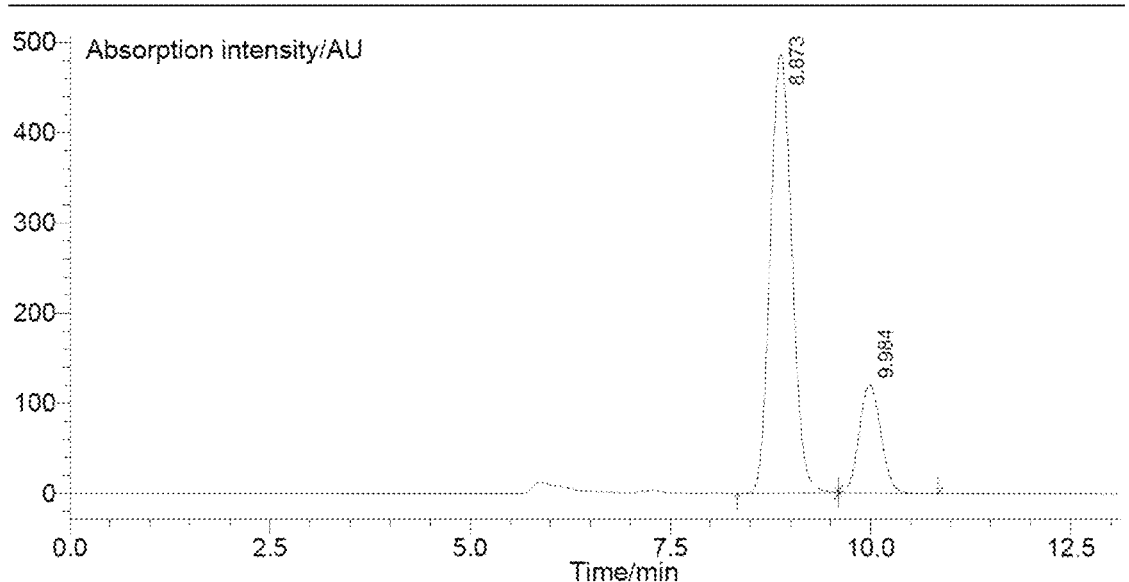
FIG. 5 is a HPLC graph of BDQ in a crude product prepared in Example 1 of the present disclosure.

FIG. 5 showed HPLC graph of BDQ in the crude product obtained from Example 1, and peak area and retention time were shown in Table 2 below.

TABLE 2

Peak area and retention time data of BDQ obtained in Example 1

| Peak No. | Retention time | Area | Height | Area % | Height % |
|---|---|---|---|---|---|
| 1 | 8.873 | 9138489 | 486722 | 80.269 | 80.212% |
| 2 | 9.984 | 2246363 | 120071 | 19.731 | 19.788 |
| Total | | 11384851 | 606794 | 100.000 | 100.000 |

The ee value of BDQ obtained in Example 1 was 60%.

Figure 6:
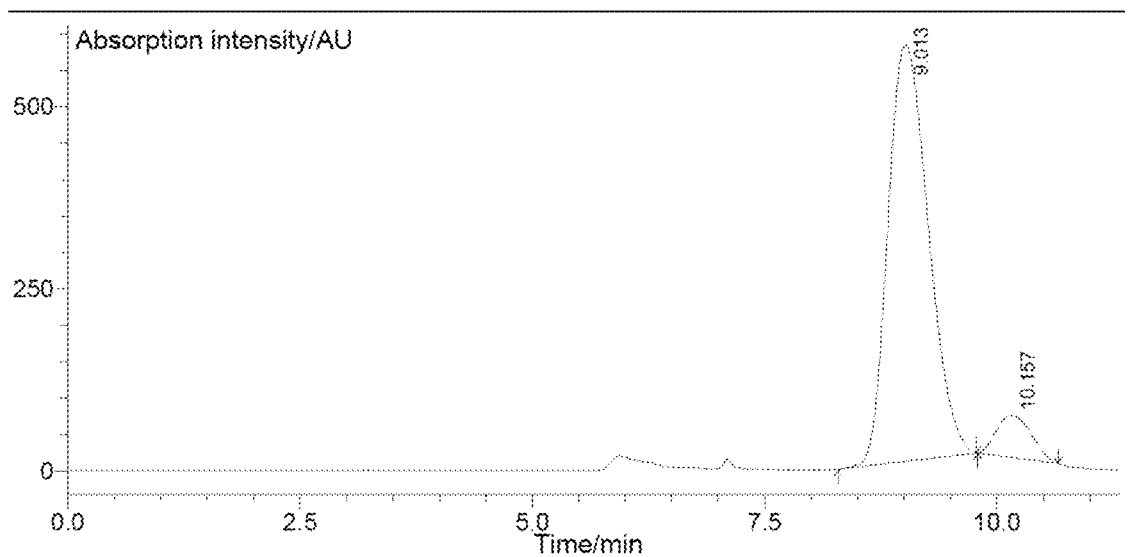
FIG. 6 is a HPLC graph of BDQ in a crude product prepared in Example 2 of the present disclosure.

FIG. 6 showed HPLC graph of BDQ in the crude product obtained from Example 2, and peak area and retention time were shown in Table 3 below.

TABLE 3

Peak area and retention time data for BDQ obtained in Example 2

| Peak No. | Retention time | Area | Height | Area % | Height % |
|---|---|---|---|---|---|
| 1 | 9.013 | 17288014 | 571187 | 91.979 | 90.903 |
| 2 | 10.157 | 1507515 | 57161 | 8.021 | 9.097 |
| Total | | 18795529 | 628348 | 100.000 | 100.000 |

The ee value of BDQ obtained in Example 2 was 8400.

Figure 7:
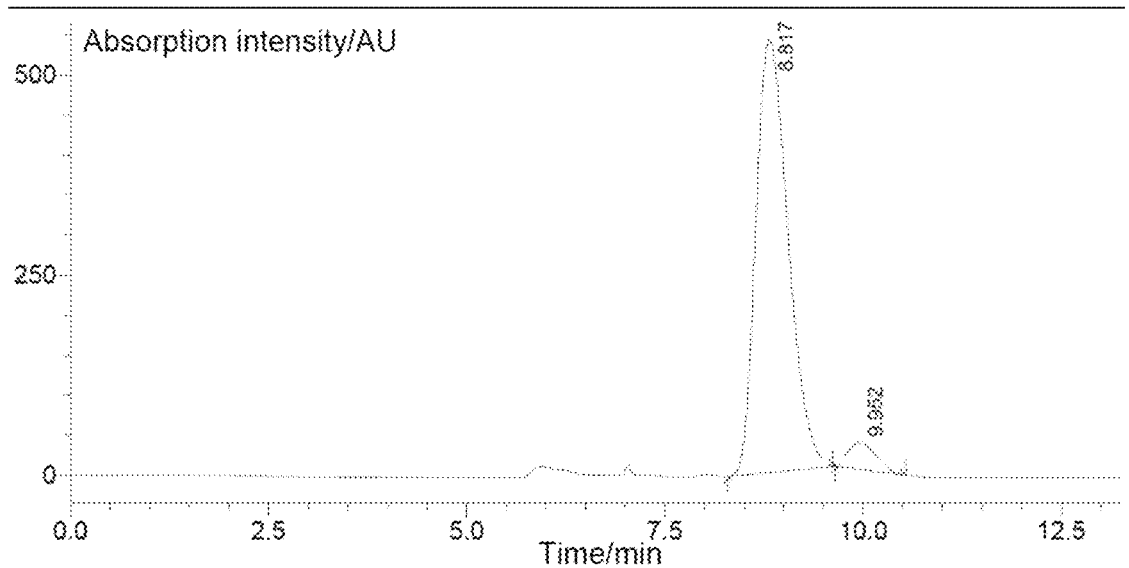
FIG. 7 is a HPLC graph of BDQ in a crude product prepared in Example 3 of the present disclosure.

FIG. 7 showed HPLC graph of BDQ in the crude product obtained from Example 3, and peak area and retention time were shown in Table 4 below.

TABLE 4

Peak area and retention time data for BDQ obtained in Example 3

| Peak No. | Retention time | Area | Height | Area % | Height% |
|---|---|---|---|---|---|
| 1 | 8.817 | 15258405 | 540209 | 95.007 | 94.229 |
| 2 | 9.952 | 801922 | 33083 | 4.993 | 5.771 |
| Total | | 16060326 | 573292 | 100.000 | 100.000 |

The ee value of BDQ obtained in Example 3 was 900%.

Figure 8:
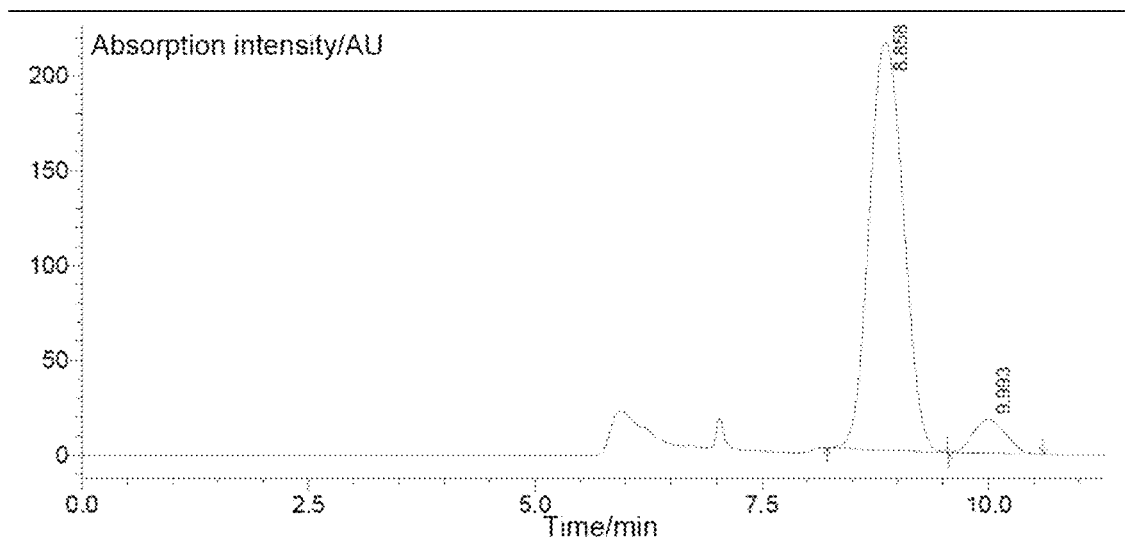
FIG. 8 is a HPLC graph of BDQ in a crude product prepared in Example 4 of the present disclosure.

FIG. 8 showed HPLC graph of BDQ in the crude product obtained in Example 4, and peak area and retention time were shown in Table 5 below.

TABLE 5

Peak area and retention time data for BDQ obtained in Example 4

| Peak No. | Retention time | Area | Height | Area % | Height% |
|---|---|---|---|---|---|
| 1 | 8.858 | 5661095 | 215400 | 92.634 | 92.384 |
| 2 | 9.993 | 450182 | 17757 | 7.366 | 7.616 |
| Total | | 6111278 | 233157 | 100.000 | 100.000 |

The ee value of BDQ obtained in Example 4 was 860%.

Figure 9:
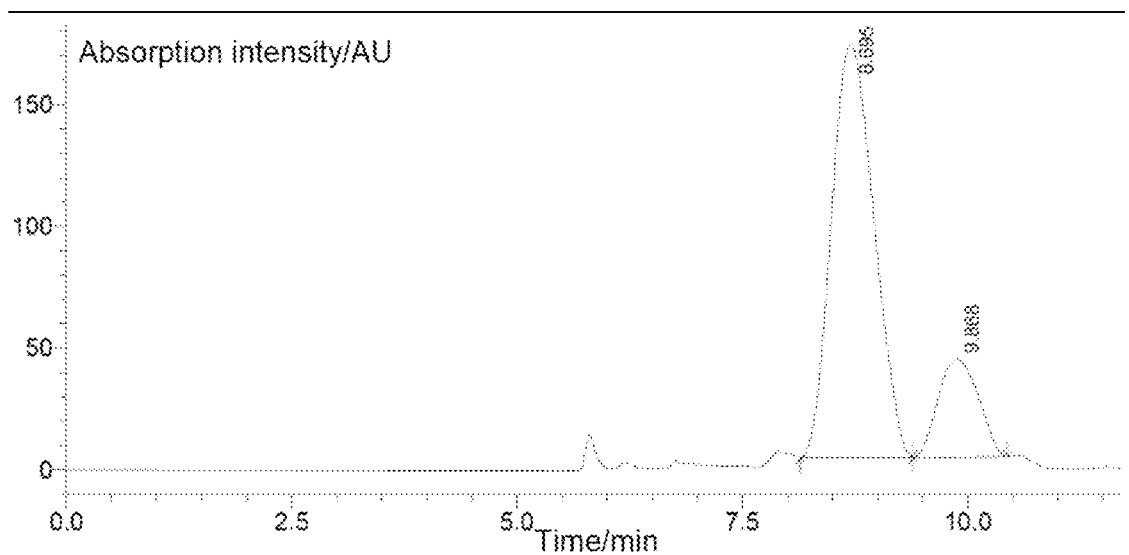
FIG. 9 is a HPLC graph of BDQ in a crude product prepared in Example 5 of the present disclosure.

FIG. 9 showed HPLC graph of BDQ in the crude product obtained in Example 5, and peak area and retention time were shown in Table 6 below.

TABLE 6

Peak area and retention time data for BDQ obtained in Example 5

| Peak No. | Retention time | Area | Height | Area % | Height% |
|---|---|---|---|---|---|
| 1 | 8.695 | 5574827 | 169867 | 81.613 | 80.797 |
| 2 | 9.868 | 1255987 | 40373 | 18.387 | 19.203 |
| Total | | 6830814 | 210240 | 100.000 | 100.000 |

The ee value of BDQ obtained in Example 5 was 630%.

Figure 10:
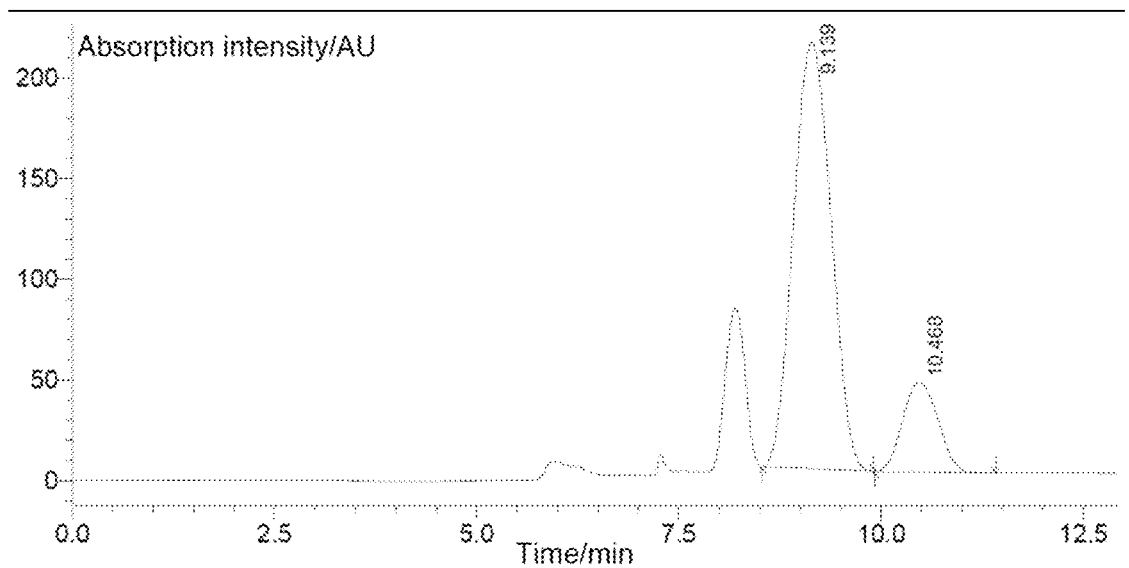
FIG. 10 is a HPLC graph of BDQ in a crude product prepared in Example 6 of the present disclosure.

FIG. 10 showed HPLC graph of BDQ in the crude product obtained in Example 6, and peak area and retention time were shown in Table 7 below.

TABLE 7

Peak area and retention time data for BDQ obtained in Example 6

| Peak No. | Retention time | Area | Height | Area % | Height% |
|---|---|---|---|---|---|
| 1 | 9.139 | 6849467 | 211606 | 83.611 | 82.754 |
| 2 | 10.468 | 1342631 | 44099 | 16.389 | 17.246 |
| Total | | 8192098 | 255704 | 100.000 | 100.000 |

The ee value of BDQ was measured to be 68% in Example 6.

The ee value of BDQ obtained from Examples 7-21 was measured using the same method described above, and the results were as described previously.

Experimental Example 2

The purity of BDQ after post-treatment of the mixtures obtained in Examples 1-21 was determined.

Chromatographic Conditions:

The chromatographic column was a ChiralpakAD-H chiral column from Daicel Corp, Japan. The HPLC Instrument was LC-2010 from Shimadzu Corporation.

Mobile phase: chromatographically pure isopropanol and n-hexane

Flow rate: 0.5 mL/min

Hexane/i-PrOH=98/2

Detection wavelength: 230 nm

Figure 11:
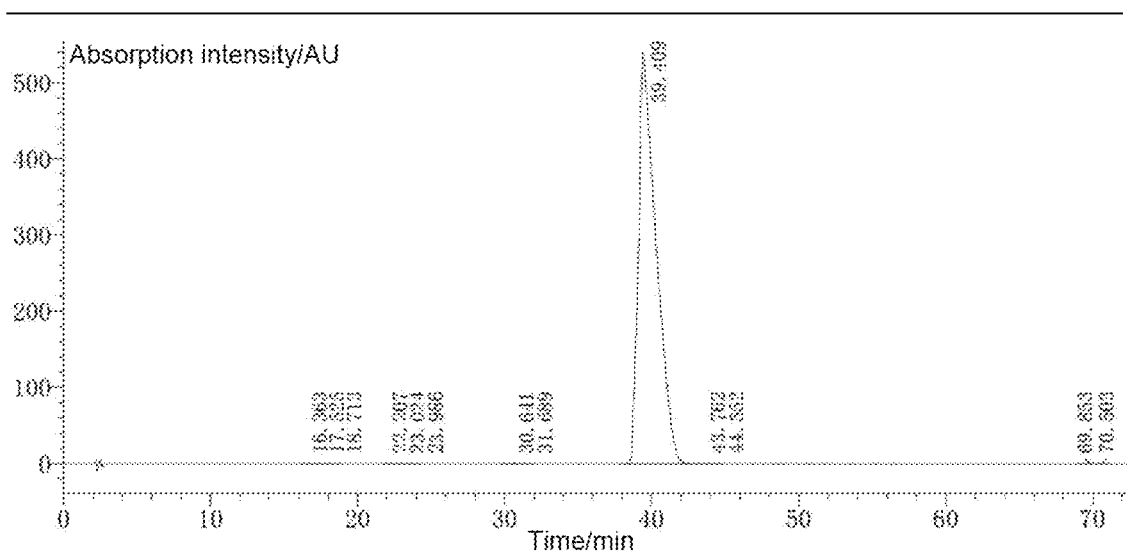
FIG. 11 is a HPLC graph of a product obtained from the crude product prepared in Example 1 of the present disclosure through recrystallisation.

FIG. 11 was a graph of the product obtained in Example 1 after recrystallisation, and the peak area and retention time were shown in Table 8 below. According to Table 8, peak number 9 represented BDQ with a purity of 99.864%, and the impurities associated with the synthesis of BDQ were all less than 0.1%.

TABLE 8

Peak area and retention time data for the product obtained in Example 1 after recrystallisation.

| Peak No. | Retention time | Height | Area | Area % |
|---|---|---|---|---|
| 1 | 16.363 | 157 | 3817 | 0.008 |
| 2 | 17.525 | 197 | 4499 | 0.010 |
| 3 | 18.713 | 99 | 2596 | 0.006 |
| 4 | 22.207 | 90 | 1630 | 0.004 |
| 5 | 23.024 | 182 | 5075 | 0.011 |
| 6 | 23.986 | 95 | 1837 | 0.004 |
| 7 | 30.641 | 361 | 16913 | 0.038 |
| 8 | 31.689 | 148 | 5239 | 0.012 |
| 9 | 39.409 | 538360 | 45029123 | 99.864 |
| 10 | 43.762 | 148 | 6070 | 0.013 |
| 11 | 44.552 | 95 | 1749 | 0.004 |
| 12 | 69.853 | 130 | 5927 | 0.013 |
| 13 | 70.503 | 151 | 6089 | 0.014 |
| Total | | 540214 | 45090563 | 100.000 |

Described above are merely preferred embodiments of the disclosure, which are not intended to limit the disclosure. It should be understood that any modifications and replacements made by those skilled in the art without departing from the spirit of the disclosure should fall within the scope of the disclosure defined by the appended claims.

What is claimed is:

1. A continuous-flow preparation method of bedaquiline, comprising:
   (a) subjecting a first feed liquid and a second feed liquid to a first continuous flow reaction for 30-600 seconds to obtain a first reaction mixture;

wherein the first feed liquid is a mixture of (1S,2R)-2-amino-1, 2-diphenylethanol, N-methylpiperazine, butyllithium, lithium chloride, and tetrahydrofuran; and the second feed liquid is a mixture of 6-bromo-3-benzyl-2-methoxyquinoline and tetrahydrofuran;

(b) subjecting the first reaction mixture and a third feed liquid to a second continuous flow reaction for 30-600 seconds to obtain a second reaction mixture;

wherein the third feed liquid is a mixture of 3-dimethylamino-1-naphthyl-1-acetone and tetrahydrofuran; and (c) quenching the second reaction mixture.

2. The continuous-flow preparation method of claim 1, wherein at least one of the first continuous flow reaction and the second continuous flow reaction is carried out in a continuous flow reactor, and the continuous flow reactor is a reaction tube;

the first continuous flow reaction is carried out for 30-90 s or 180-600 s; and/or the second continuous flow reaction is carried out for 30-60 s or 120-360 s.

3. The continuous-flow preparation method of claim 1, wherein the first continuous flow reaction is carried out at −80° C. to 0° C.;

the second continuous flow reaction is carried out at −80° C. to 0° C.; and/or the quenching is performed at −80° C. to 0° C.

4. The continuous-flow preparation method of claim 3, wherein the first continuous flow reaction is carried out at −80° C. to −10° C.;

the second continuous flow reaction is carried out at −80° C. to −20° C.; and/or the quenching is performed at −60° C. to 0° C.

5. The continuous-flow preparation method of claim 1, wherein a flow rate of the first feed liquid is 10-500 mL/min;

a flow rate of the second feed liquid is 10-500 mL/min; and/or a flow rate of the third feed liquid is 10-500 mL/min.

6. The continuous-flow preparation method of claim 5, wherein the flow rate of the first feed liquid is 10-200 mL/min;

a flow rate of the second feed liquid is 10-200 mL/min; and/or a flow rate of the third feed liquid is 10-200 mL/min.

7. The continuous-flow preparation method of claim 1, wherein in step (c), the second reaction mixture is quenched with a quenching reagent in a quenching device, wherein the quenching device is not a continuous flow reactor; and the quenching reagent is an ammonium chloride solution; or the second reaction mixture obtained in step (b) and a fourth feed liquid are subjected to a continuous quenching reaction; wherein the fourth feed liquid is a quenching solvent with a flow rate of 10-500 mL/min; and the quenching solvent is a protic solvent selected from the group consisting of methanol, ethanol and a combination thereof.

8. The continuous-flow preparation method of claim 1, wherein a ratio of the number of moles of (1S,2R)-2-amino-1, 2-diphenylethanol to a volume of tetrahydrofuran in the first feed liquid is 0.1-0.7 mol/L;

a ratio of the number of moles of N-methylpiperazine to the volume of tetrahydrofuran in the first feed liquid is 0.1-0.7 mol/L;

a ratio of the number of moles of lithium chloride to the volume of tetrahydrofuran in the first feed liquid is 0.1-0.8 mol/L;

a ratio of the number of moles of butyllithium to the volume of tetrahydrofuran in the first feed liquid is 0.4-1.2 mol/L;

a ratio of the number of moles of 6-bromo-3-benzyl-2-methoxyquinoline to a volume of tetrahydrofuran in the second feed liquid is 0.04-1.0 mol/L;

a ratio of the number of moles of 3-dimethylamino-1-naphthyl-1-acetone to a volume of tetrahydrofuran in the third feed liquid is 0.04-1.0 mol/L; and/or a molar ratio of N-methylpiperazine to 6-bromo-3-benzyl-2-methoxyquinoline is 0.5-5.0:1.

9. The continuous-flow preparation method of claim 1, wherein a molar ratio of (1S,2R)-2-amino-1, 2-diphenylethanol to 6-bromo-3-benzyl-2-methoxyquinoline is 0.8-5.0:1;

a molar ratio of lithium chloride to 6-bromo-3-benzyl-2-methoxyquinoline is 0.8-5.0:1;

a molar ratio of butyllithium to 6-bromo-3-benzyl-2-methoxyquinoline is 1.0-10.0:1; and/or a molar ratio of 3-dimethylamino-1-naphthyl-1-propanone to 6-bromo-3-benzyl-2-methoxyquinoline is 0.8-5.0:1.

10. The continuous-flow preparation method of claim 1, wherein after the step (c), the continuous-flow preparation method further comprises a post-treatment comprising extraction, crystallisation and pulping;

wherein a recrystallisation solvent and a pulping solvent are independently selected from the group consisting of toluene, ethyl acetate, hexane, ethanol, isopropanol, benzene, isopropyl ether, and a combination thereof.

11. The continuous-flow preparation method of claim 10, wherein the recrystallisation is performed through steps of:

removing an extraction solvent to obtain a filtrate; and preparing a saturated solution of the filtrate with the recrystallisation solvent following by crystallization to obtain a diastereoisomer of bedaquiline.

12. The continuous-flow preparation method of claim 11, wherein the extraction solvent is removed through steps of:

subjecting an organic phase collected after the extraction to rotary evaporation until a solid is precipitated, and filtration to obtain the filtrate;

the crystallization is performed through steps of:

cooling the saturated solution at −20-0° C. to form a supersaturated solution to allow precipitation of crystals followed by filtering and rotary evaporation to remove the recrystallisation solvent; and after the rotary evaporation, a pure bedaquiline product is obtained by pulping.

* * * * *